United States Patent
Ribble et al.

(10) Patent No.: US 10,395,769 B2
(45) Date of Patent: Aug. 27, 2019

(54) PATIENT CARE DEVICES WITH LOCAL INDICATION OF CORRESPONDENCE AND POWER LINE INTERCONNECTIVITY

(71) Applicant: Hill-Rom Services, Inc., Batesville, IN (US)

(72) Inventors: David L. Ribble, Indianapolis, IN (US); Steven A. Dixon, Riverview, FL (US)

(73) Assignee: Hill-Rom Services, Inc., Batesville, IN (US)

(*) Notice: Subject to any disclaimer, the term of this patent is extended or adjusted under 35 U.S.C. 154(b) by 117 days.

(21) Appl. No.: 15/379,572

(22) Filed: Dec. 15, 2016

(65) Prior Publication Data

US 2017/0177816 A1 Jun. 22, 2017

Related U.S. Application Data

(60) Provisional application No. 62/268,016, filed on Dec. 16, 2015.

(51) Int. Cl.
*G16H 40/63* (2018.01)
*A61G 7/05* (2006.01)
*G08B 5/38* (2006.01)
*A61B 90/90* (2016.01)

(52) U.S. Cl.
CPC ............. *G16H 40/63* (2018.01); *A61B 90/90* (2016.02); *A61G 7/05* (2013.01); *G08B 5/38* (2013.01); *A61G 2205/60* (2013.01)

(58) Field of Classification Search
CPC .......... G16H 40/63; G06F 19/00; G08B 5/38; A61B 90/90; A61G 7/05; A61G 2205/60
See application file for complete search history.

(56) References Cited

U.S. PATENT DOCUMENTS

| | | |
|---|---|---|
| 2,740,873 A | 4/1956 | Cronk |
| 2,858,421 A | 10/1958 | Touvet |
| 3,953,933 A | 5/1976 | Goldstein |
| 3,987,928 A | 10/1976 | Mori |
| 4,343,411 A | 8/1982 | Chesnut et al. |

(Continued)

FOREIGN PATENT DOCUMENTS

| | | |
|---|---|---|
| DE | 197 01 603 A1 | 7/1998 |
| DE | 199 12 395 A1 | 9/2000 |

(Continued)

OTHER PUBLICATIONS

ST7540 FSK power line transceiver, 2006 STMicroelectronics, 43 pages.

(Continued)

*Primary Examiner* — James J Yang
(74) *Attorney, Agent, or Firm* — Barnes & Thornburg LLP

(57) ABSTRACT

According to the present disclosure, a system includes a patient support device and a power line network for communicating data, such as patient identifying information. The patient support device locally indicates information about an assigned patient. A patient care apparatus is communicatively connected to the power line network to receive data and to provide a local indication of the data received. The local indication of the device and the apparatus includes respective lights that flash substantially synchronously.

18 Claims, 3 Drawing Sheets

(56)  References Cited

U.S. PATENT DOCUMENTS

| | | | |
|---|---|---|---|
| 4,465,333 A | 8/1984 | Caserta et al. | |
| 4,678,264 A | 7/1987 | Bowen et al. | |
| 4,721,358 A | 1/1988 | Faber et al. | |
| 4,767,168 A | 8/1988 | Grandy | |
| 4,767,181 A | 8/1988 | McEowen | |
| 4,835,343 A | 5/1989 | Graef et al. | |
| 4,844,582 A | 7/1989 | Giannini | |
| 4,903,340 A | 2/1990 | Sorensen | |
| 4,924,349 A | 5/1990 | Buehler et al. | |
| 4,977,619 A | 12/1990 | Crimmins | |
| 4,984,297 A | 1/1991 | Manome | |
| 5,033,112 A | 7/1991 | Bowling et al. | |
| 5,049,876 A | 9/1991 | Kahle et al. | |
| 5,060,303 A | 10/1991 | Wilmoth | |
| 5,073,681 A | 12/1991 | Hubben et al. | |
| 5,089,974 A | 2/1992 | Demeyer et al. | |
| 5,099,346 A | 3/1992 | Lee et al. | |
| 5,103,108 A | 4/1992 | Crimmins | |
| 5,109,452 A | 4/1992 | Selvin et al. | |
| 5,140,659 A | 8/1992 | Minds et al. | |
| 5,146,528 A | 9/1992 | Gleim et al. | |
| 5,180,886 A | 1/1993 | Dierenbach et al. | |
| 5,212,760 A | 5/1993 | Goetz | |
| 5,214,526 A | 5/1993 | Tonomura | |
| 5,242,315 A | 9/1993 | O'Dea | |
| 5,247,380 A | 9/1993 | Lee et al. | |
| 5,274,490 A | 12/1993 | Tsushima et al. | |
| 5,278,536 A | 1/1994 | Furtaw et al. | |
| 5,305,132 A | 4/1994 | Fasen et al. | |
| 5,305,133 A | 4/1994 | Cooper et al. | |
| 5,321,542 A | 6/1994 | Freitas et al. | |
| 5,416,627 A | 5/1995 | Wilmoth | |
| 5,456,373 A | 10/1995 | Ford | |
| 5,477,010 A | 12/1995 | Buckshaw et al. | |
| 5,508,836 A | 4/1996 | DeCaro et al. | |
| 5,548,654 A | 8/1996 | Fast | |
| 5,561,412 A | 10/1996 | Novak et al. | |
| 5,579,001 A | 11/1996 | Dempsey et al. | |
| 5,594,786 A | 1/1997 | Chaco et al. | |
| 5,596,648 A | 1/1997 | Fast | |
| 5,617,236 A | 4/1997 | Wang et al. | |
| 5,657,201 A | 8/1997 | Kochis | |
| 5,675,125 A | 10/1997 | Hollinger | |
| 5,696,861 A | 12/1997 | Schimmeyer et al. | |
| 5,699,038 A | 12/1997 | Ulrich et al. | |
| 5,706,110 A | 1/1998 | Nykanen | |
| 5,723,817 A | 3/1998 | Arenas et al. | |
| 5,811,729 A | 9/1998 | Rintz | |
| 5,811,730 A | 9/1998 | Rintz | |
| 5,813,873 A | 9/1998 | McBain et al. | |
| 5,838,223 A | 11/1998 | Gallant et al. | |
| 5,838,471 A | 11/1998 | Beard | |
| 5,874,693 A | 2/1999 | Rintz | |
| 5,877,820 A | 3/1999 | Yamamuro et al. | |
| 5,895,888 A | 4/1999 | Arenas et al. | |
| 5,907,419 A | 5/1999 | Martnelli et al. | |
| 5,910,776 A | 6/1999 | Black | |
| 5,949,567 A | 9/1999 | Jebens | |
| 5,967,840 A | 10/1999 | Rose et al. | |
| 5,982,519 A | 11/1999 | Martnelli et al. | |
| 5,994,998 A | 11/1999 | Fisher et al. | |
| 5,995,253 A | 11/1999 | Flaherty | |
| 5,998,735 A | 12/1999 | Patterson, Jr. | |
| 6,051,787 A | 4/2000 | Rintz | |
| 6,071,015 A | 6/2000 | Erbse et al. | |
| 6,117,076 A | 9/2000 | Cassidy | |
| 6,140,911 A | 10/2000 | Fisher et al. | |
| 6,147,592 A | 11/2000 | Ulrich et al. | |
| 6,183,101 B1 | 2/2001 | Chien | |
| 6,193,655 B1 | 2/2001 | McGrath | |
| 6,259,355 B1 | 7/2001 | Chaco et al. | |
| 6,281,440 B1 | 8/2001 | Baldwin et al. | |
| 6,304,600 B1 | 10/2001 | Chiba | |
| 6,329,906 B1 | 12/2001 | Fisher et al. | |
| 6,355,885 B1 | 3/2002 | Rintz et al. | |
| 6,362,725 B1 | 3/2002 | Ulrich et al. | |
| 6,434,187 B1 | 8/2002 | Beard et al. | |
| 6,442,145 B1 | 8/2002 | De Lange et al. | |
| 6,445,299 B1 | 9/2002 | Rojas, Jr. | |
| 6,457,874 B1 | 10/2002 | Clapp, Jr. et al. | |
| 6,486,792 B1 | 11/2002 | Moster et al. | |
| 6,493,121 B1 | 12/2002 | Althaus | |
| 6,496,105 B2 | 12/2002 | Fisher et al. | |
| 6,500,026 B2 | 12/2002 | Yamaguchi | |
| 6,504,633 B1 | 1/2003 | Hovorka et al. | |
| 6,504,635 B1 | 1/2003 | Nakashima | |
| 6,514,652 B2 | 2/2003 | Cash, Jr. | |
| 6,533,466 B1 | 3/2003 | Smith | |
| 6,544,075 B1 | 4/2003 | Liao | |
| 6,544,200 B1 | 4/2003 | Smith et al. | |
| 6,545,218 B1 | 4/2003 | Blaess | |
| 6,552,888 B2 | 4/2003 | Weinberger | |
| 6,558,045 B2 | 5/2003 | Yamaguchi | |
| 6,563,618 B1 | 5/2003 | Morrow et al. | |
| 6,585,431 B1 | 7/2003 | Okamoto | |
| 6,599,025 B1 | 7/2003 | Deutsch | |
| 6,608,253 B1 | 8/2003 | Rintz | |
| 6,609,166 B1 | 8/2003 | Nakashima | |
| 6,659,947 B1 | 12/2003 | Carter et al. | |
| 6,668,328 B1 | 12/2003 | Bell | |
| 6,688,779 B2 | 2/2004 | Nishita | |
| 6,710,704 B2 | 3/2004 | Fisher et al. | |
| 6,721,980 B1 | 4/2004 | Price et al. | |
| 6,753,761 B2 | 6/2004 | Fisher et al. | |
| 6,763,195 B1 | 7/2004 | Willebrand et al. | |
| 6,897,780 B2 | 5/2005 | Ulrich et al. | |
| 6,989,735 B2 | 1/2006 | Fisher et al. | |
| 7,039,456 B2 | 5/2006 | Chen | |
| 7,068,143 B2 | 6/2006 | Doering et al. | |
| 7,150,655 B2 | 12/2006 | Mastrototaro et al. | |
| 7,155,622 B2 | 12/2006 | Mancey et al. | |
| 7,177,673 B2 | 2/2007 | Matsumura et al. | |
| 7,242,308 B2 | 7/2007 | Ulrich et al. | |
| 7,244,150 B1 | 7/2007 | Brase et al. | |
| 7,319,386 B2 | 1/2008 | Collins, Jr. et al. | |
| 7,330,127 B2 | 2/2008 | Price et al. | |
| 7,399,205 B2 | 7/2008 | McNeely et al. | |
| 7,484,963 B2 | 2/2009 | Fenwick et al. | |
| 7,515,059 B2 | 4/2009 | Price et al. | |
| 7,538,659 B2 | 5/2009 | Ulrich et al. | |
| 7,746,218 B2 | 6/2010 | Collins, Jr. et al. | |
| 2002/0004336 A1 | 1/2002 | Yamaguchi | |
| 2002/0012329 A1 | 1/2002 | Atkinson et al. | |
| 2002/0014951 A1 | 2/2002 | Kramer et al. | |
| 2002/0021209 A1 | 2/2002 | Fisher et al. | |
| 2002/0023121 A1 | 2/2002 | Sugiyama et al. | |
| 2002/0032812 A1 | 3/2002 | Ito | |
| 2002/0039068 A1 | 4/2002 | Holowick | |
| 2002/0060617 A1 | 5/2002 | Walbeck et al. | |
| 2002/0060624 A1 | 5/2002 | Zhang | |
| 2002/0067282 A1 | 6/2002 | Moskowitz et al. | |
| 2002/0091843 A1 | 7/2002 | Vald | |
| 2002/0101349 A1 | 8/2002 | Rojas, Jr. | |
| 2002/0101861 A1 | 8/2002 | Gancarcik et al. | |
| 2002/0142650 A1 | 10/2002 | Clark et al. | |
| 2002/0149822 A1 | 10/2002 | Stroud | |
| 2002/0151990 A1 | 10/2002 | Ulrich et al. | |
| 2002/0179092 A1 | 12/2002 | Swennen et al. | |
| 2003/0006881 A1 | 1/2003 | Reyes | |
| 2003/0016419 A1 | 1/2003 | Palmer et al. | |
| 2003/0025601 A1 | 2/2003 | Gruteser et al. | |
| 2003/0039257 A1* | 2/2003 | Manis | H04B 3/54 370/400 |
| 2003/0052770 A1 | 3/2003 | Mansfield, Jr. et al. | |
| 2003/0052787 A1 | 3/2003 | Zerhusen et al. | |
| 2003/0058085 A1 | 3/2003 | Fisher et al. | |
| 2003/0062990 A1 | 4/2003 | Schaeffer, Jr. et al. | |
| 2003/0062991 A1 | 4/2003 | Fisher et al. | |
| 2003/0153387 A1 | 8/2003 | Small et al. | |
| 2003/0185515 A1 | 10/2003 | Lubkert et al. | |
| 2003/0210770 A1 | 11/2003 | Krejcarek | |
| 2003/0223756 A1 | 12/2003 | Tatum et al. | |
| 2003/0227900 A1 | 12/2003 | Watanabe | |
| 2004/0024913 A1 | 2/2004 | Ikeda et al. | |

(56) References Cited

U.S. PATENT DOCUMENTS

| | | |
|---|---|---|
| 2004/0091270 A1 | 5/2004 | Choi et al. |
| 2005/0033124 A1 | 2/2005 | Kelly et al. |
| 2006/0038660 A1 | 2/2006 | Doumuki et al. |
| 2006/0049936 A1 | 3/2006 | Collins et al. |
| 2007/0135866 A1 | 6/2007 | Baker et al. |
| 2007/0141869 A1 | 6/2007 | McNeely et al. |
| 2007/0159772 A1 | 7/2007 | Morice |
| 2007/0210917 A1 | 9/2007 | Collins et al. |
| 2008/0094207 A1 | 4/2008 | Collins et al. |
| 2008/0205311 A1 | 8/2008 | Perkins et al. |
| 2008/0224861 A1 | 9/2008 | McNeely et al. |
| 2009/0063183 A1 | 3/2009 | McNeely et al. |
| 2009/0112630 A1 | 4/2009 | Collins et al. |
| 2009/0212925 A1 | 8/2009 | Schuman, Sr. et al. |
| 2009/0212956 A1 | 8/2009 | Schuman et al. |
| 2009/0214009 A1 | 8/2009 | Schuman, Sr. et al. |
| 2009/0217080 A1 | 8/2009 | Ferguson et al. |
| 2010/0040241 A1 | 2/2010 | Sowada |
| 2010/0079276 A1 | 4/2010 | Collins et al. |
| 2010/0101022 A1 | 4/2010 | Riley et al. |
| 2010/0125952 A1 | 5/2010 | Frondorf et al. |
| 2013/0069771 A1 | 3/2013 | Frondorf |
| 2013/0135160 A1* | 5/2013 | Dixon ............... H01Q 1/44 343/720 |
| 2014/0236629 A1 | 8/2014 | Kim et al. |
| 2014/0248804 A1* | 9/2014 | McNeely ............ A61B 5/0006 439/620.21 |
| 2014/0313700 A1* | 10/2014 | Connell ................. A61G 7/05 362/130 |

FOREIGN PATENT DOCUMENTS

| | | |
|---|---|---|
| DE | 200 15 392 U1 | 5/2001 |
| EP | 0 529 926 A1 | 3/1993 |
| WO | WO 2000/37978 | 6/2000 |
| WO | WO 2005/022692 | 3/2005 |

OTHER PUBLICATIONS

Maxim Integrated Powerline Digital Transceiver, Maxim Integrated Products, 2004, 28 pages.

Maxim MAX2992 G3-PLC MAC/PHY Powerline Transceiver, 2 pages.

Cypress Perform, Powerline Transceiver Data Sheet, Cypress Semiconductor Corporation, Oct. 20, 2009, 40 pages.

\* cited by examiner though the first and second indicator modules are configured to receive at least one signal indicative of patient IDs and to operate their respective first and second indicators to communicate patterns that are substantially synchronous to each other when the first and second indicator modules receive at least one signal indicative of the same patient ID to provide a cue that the patient support device and the patient care apparatus are each associated with the same patient.

PATIENT CARE DEVICES WITH LOCAL INDICATION OF CORRESPONDENCE AND POWER LINE INTERCONNECTIVITY

The present application claims the benefit, under 35 U.S.C. § 119(e), of U.S. Provisional Application No. 62/268,016, which was filed Dec. 16, 2015 and which is hereby incorporated by reference herein in its entirety.

BACKGROUND

The present disclosure relates to patient care devices of a care facility. More specifically, the present disclosure relates to patient care devices with local indicators and data interconnection between care devices.

Confirming that information is accurately shared can assist in identifying misinformation in care facility operations. However, caregivers are often burdened with demanding schedules. Time consuming tasks, such as confirming patient information, can add stress to the caregiver which can ultimately affect patients. Providing ease of access and confirmation of information can reduce the caregiver's burden.

SUMMARY

The present application discloses one or more of the features recited in the appended claims and/or the following features which, alone or in any combination, may comprise patentable subject matter:

According to an aspect of the disclosure, a patient care device may include a patient support device, a power line network that may include an ID source device configured to receive a patient ID associated with a patient assigned to the patient support device and to communicate the patient ID throughout the power line network, an electric power distribution circuit configured to provide electric power to the patient support device, and at least one power receptacle connected to receive electric power from the electric power distribution circuit, and the power line network communicates the patient ID by configuration of the electric power distribution circuit to supply electric power to operate devices connected to the at least one power receptacle.

In some embodiments, the ID source device may include a power line transceiver.

In some embodiments, the ID source device may communicate the patient ID throughout the power line network through a modulated carrier signal embedded within the electrical power provided by the electrical power distribution circuit.

In some embodiments, the patient support device may be connected for communication with a communication network and receives the patient ID associated with the patient assigned to the patient support device from the network for communication to the ID source device.

In some embodiments, the patient care device may include a patient care apparatus electrically connected to the electric power distribution circuit to receive electrical power and the patient ID therefrom over the power line network.

In some embodiments, the patient care apparatus may be electrically connected to the electric power distribution circuit by connection of a plug of the patient care apparatus to the at least one power receptacle.

In some embodiments, the at least one power receptacle may be mounted to the patient support device.

In some embodiments, the patient support device may include an indicator configured to communicate a unique pattern indicating the patient ID to provide locally observable identification of the patient ID.

In some embodiments, the indicator may include a light source configured to flash to communicate the pattern.

According to another aspect of the disclosure, a patient care system may include a patient support device, an electrically-powered patient care apparatus, and a power line network that may include an ID source device configured to receive a patient ID associated with a patient assigned to the patient support device and to communicate the patient ID throughout the power line network, an electric power distribution circuit configured to provide electric power to the patient support device and the patient care apparatus, a first power receptacle connected to receive electric power from the electric power distribution circuit, and a second power receptacle connected to receive electric power from the electric power distribution circuit, and the patient support device is electrically connected to the first receptacle and the patient care apparatus is electrically connected to the second power receptacle, and the ID source device communicates the patient ID to the patient care apparatus by configuration of the electric power distribution circuit to supply electric power to operate the patient care apparatus.

According to another aspect of the disclosure a patient care device may include a patient support device having a first indicator including a first indicator module, a patient care apparatus spaced from the patient bed and having a second indicator including a second indicator module, and a power line network that may include an ID source device configured to receive a patient ID associated with the power line network and to communicate the patient ID throughout the power line network, an electric power distribution circuit configured to provide electric power to the patient support device, and at least one power receptacle connected to receive electric power from the electric power distribution circuit, and the power line network communicates the patient ID by configuration of the electric power distribution circuit to supply electric power to the patient care apparatus when electrically connected to the at least one power receptacle, and wherein the first and second indicator modules are configured to receive at least one signal indicative of patient IDs and to operate their respective first and second indicators to communicate patterns that are substantially synchronous to each other when the first and second indicator modules receive at least one signal indicative of the same patient ID to provide a cue that the patient support device and the patient care apparatus are each associated with the same patient.

In some embodiments, the first and second indicators each may include a light source configured to flash to communicate their pattern.

In some embodiments, the patterns of the first and second indicators may include a series of light flashes that are substantially synchronous when the first and second indicator modules receive at least one signal indicating the same patient ID and substantially non-synchronous when the first and second indicator modules each receive at least one signal indicating different patient IDs.

According to another aspect of the disclosure, a patient care system may include a patient bed having a first light, and a patient care apparatus spaced from the patient bed and having a second light, the patient care apparatus being communicatively coupled to the patient bed to provide a visual cue that the patient bed and the patient care apparatus are both associated with a patient assigned to the patient bed by flashing the first and second lights substantially synchronously.

In some embodiments, the patient bed and the patient care apparatus may be communicatively coupled by a power line network configured to communicate a modulated carrier signal indicating an identification code assigned to the patient.

In some embodiments, substantially synchronous flashing of the first and second lights may indicate correspondence between an identification code known to the patient care apparatus and an identification code known to the patient bed.

Additional features alone or in combination with any other feature(s), including those listed above and those listed in the claims and those described in detail below, can comprise patentable subject matter. Others will become apparent to those skilled in the art upon consideration of the following detailed description of illustrative embodiments exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
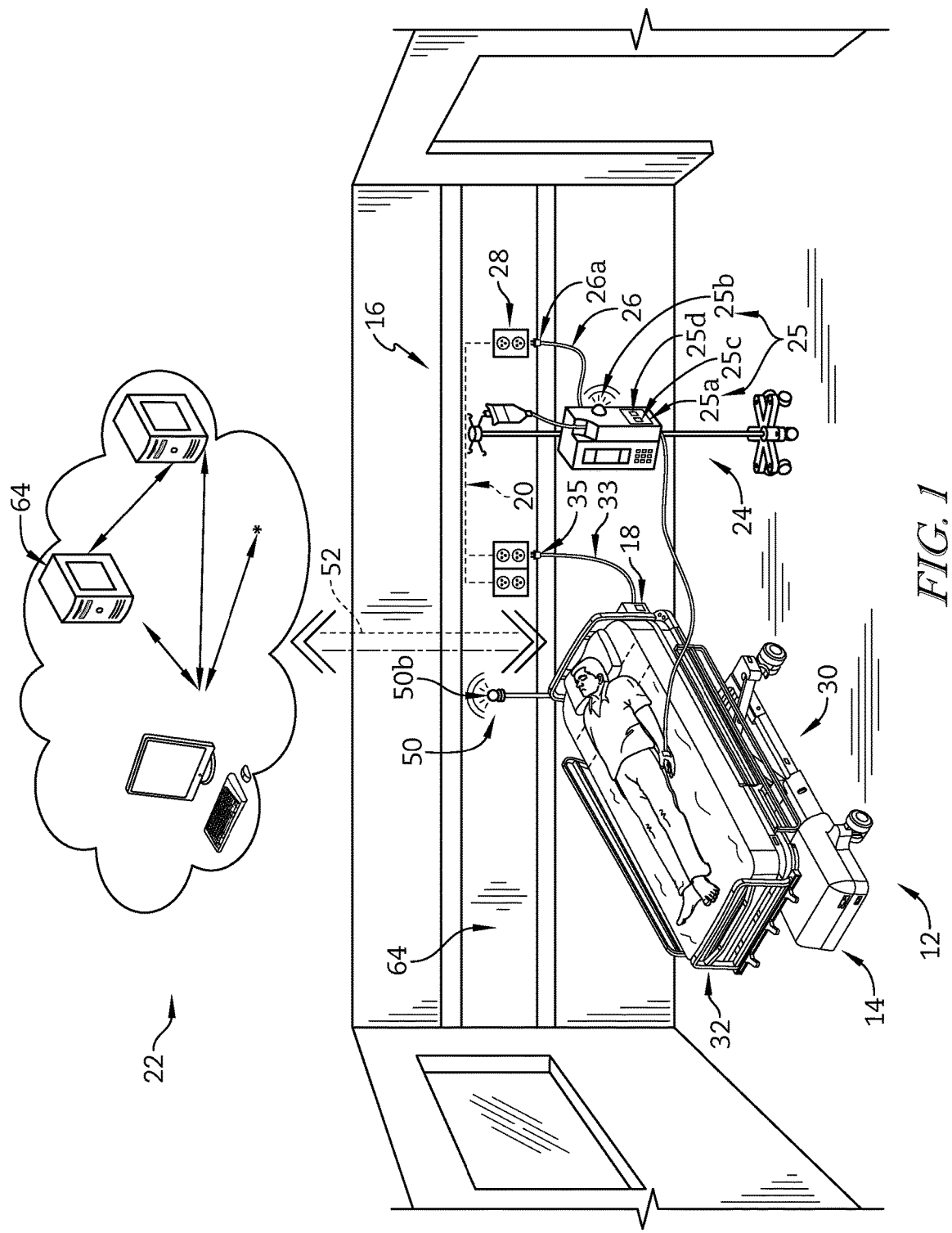
FIG. 1 is a perspective view of a patient care device including a patient support device with a first indicator that communicates a pattern based on a patient ID that is observable by persons nearby, and showing that the patient care device communicates a signal indicating the patient ID through a power line network to create a local connective network, and showing that a patient care apparatus is connected to the power line network through an electrical circuit to receive power and an indication of the patient ID and that the patient care apparatus includes a second indicator operable to communicate a pattern based on a received patient ID, and showing that the patterns of the first and second indicators are substantially synchronous to each other when they are based on the same patient ID to cue a local observer whether a corresponding information is known to the patient support device and the patient care apparatus.

A patient care system 12 illustratively includes a patient support device 14 and a power line network 16 as shown in FIG. 1. Patient support device 14 communicates data, for example, a signal indicating a patient identification ("ID") throughout power line network 16. Patient support device 14 includes an indicator 50, such as a light, operable to communicate a pattern, which in some embodiments may be a unique flashing pattern that is associated with the known patient ID of a patient occupying patient support device 14. Thus, different flashing patterns of indicators 50 on different devices 14 correspond to patients having different patient ID's. A caregiver is able to recognize correspondence between patterns of different care devices to quickly and easily confirm corresponding information and to associate the devices and information with the proper patient.

Power line network 16 illustratively includes an ID source device 18, and an electrical power circuit 20. ID source device 18 communicates a signal indicating a known patient ID throughout the power line network 16 by configuration of the electrical power circuit 20 to provide data and electrical power through common infrastructure. In the illustrative embodiment, patient support device 14 is embodied as a hospital bed and ID source device 18 is illustratively mounted on the hospital bed as shown in FIG. 1.

In the illustrative embodiment, a patient care apparatus 24 is connected to the power line network 16 to receive electrical power and data therefrom as suggested in FIG. 1. Patient care apparatus 24 is illustratively embodied as an intravenous ("IV") fluid machine for administering fluids to a patient. In the illustrative embodiment, patient care apparatus 24 is connected to the power line network 16 by connection to electrical power circuit 16 from which it receives electrical power and data, for example, a signal indicating the known patient ID. In some embodiments, patient care apparatus 24 includes any type of apparatus for patient care, for example, an assisted-respiration device such as ventilator, a feeding pump, a patient monitor, and/or any other type of patient assistance device.

In the illustrative embodiment, patient care apparatus 24 is electrically connected to electrical power circuit 20 by electrical power cord 26 as shown in FIG. 1. Plug connector 26a illustratively plugs into electrical receptacle 28 to provide electrical power to patient care apparatus 24 for operation from the electrical power circuit 20. Electrical power received by patient care apparatus 24 from power line network 16 over the electrical power circuit 20 illustratively includes at least one modulated carrier signal indicating the known patient ID. Indicator 25 of patient care apparatus 24 receives the signal indicating the flashing pattern corresponding to the patient ID from the power line network 16 and communicates the pattern based on the received signal. The pattern of indicator 25 is substantially synchronous to the pattern of indicator 50 of patient care device when the patient ID indicated by the received signal and the known patient ID of the patient support device 14 are the same. Synchronized flashing patterns provide a local cue to indicate correspondence between information (namely the patient ID) known to the patient care apparatus 24 and the patient support device 14.

In the illustrative embodiment, indicators 25, 50 each respectively include a light source 25b, 50b which illuminates at specific intervals to communicate their patterns for local observation, i.e. light sources 25b, 50b both flash at certain intervals. An observer that is local to indicators 25, 50 observes each of their communicated patterns to discern whether or not the patterns of flashes are substantially synchronous to each other. If the patterns communicated by indicators 25, 50 are substantially synchronous, the observer is cued that the patient ID known to the patient support device 14 and the patient ID known to the patient care apparatus 24 correspond. If the patterns communicated by indicators 25, 50 are not substantially synchronous, the observer is cued that the patient ID known to the patient support device 14 and the patient ID known to the patient care apparatus 24 do not correspond to each other. An observer can, therefore, easily confirm that the information known to the patient care apparatus 24 corresponds to the patient associated with the patient support device 14.

Figure 2:
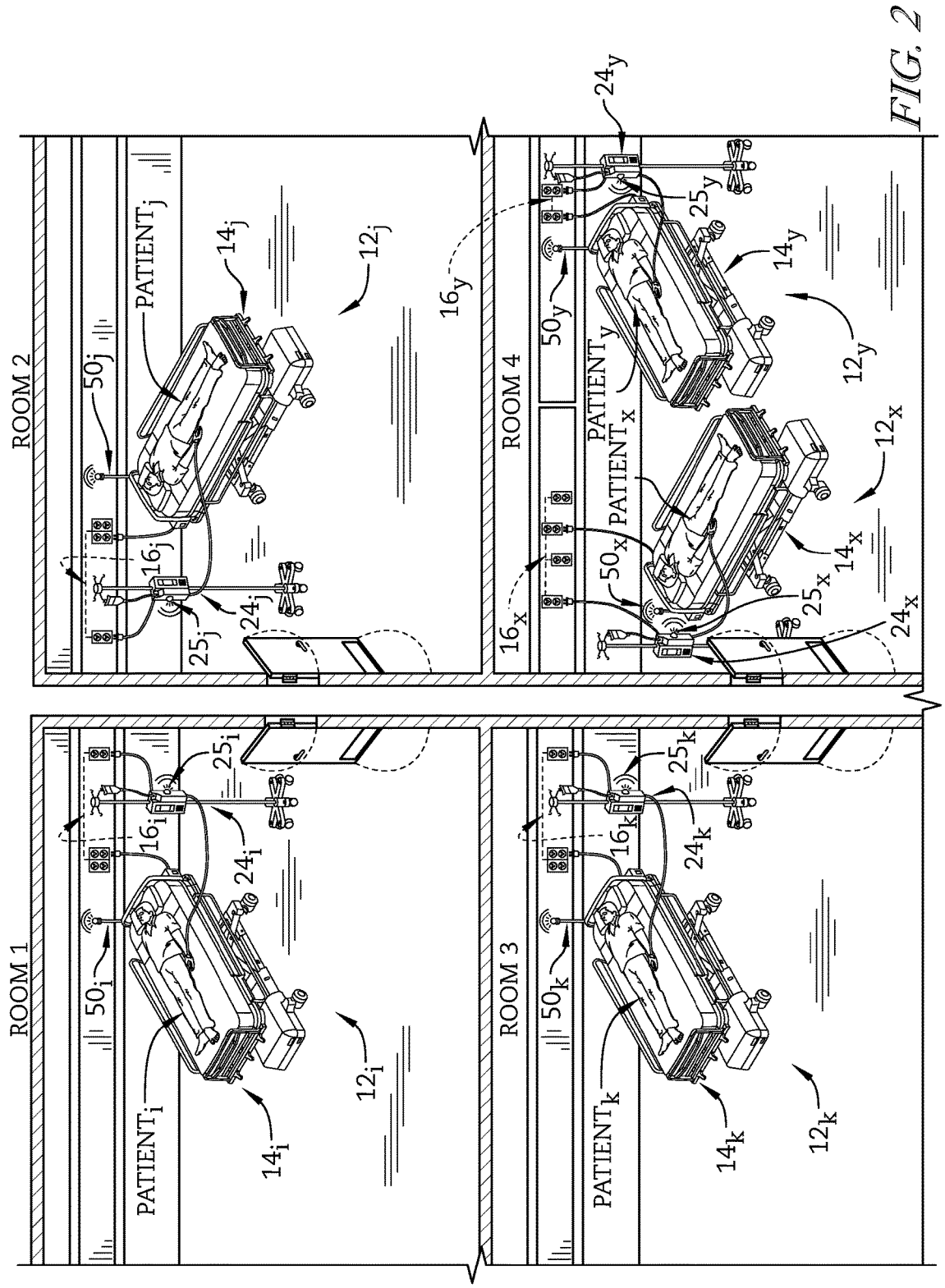
FIG. 2 is a plan view of an area of a patient care facility showing multiple patient care devices each having a distinct power line network located in patient rooms to establish distinct local connective networks and showing their respective indicators communicating patterns.

In the illustrative embodiment as shown in FIG. 2, there are four patient rooms (Rooms 1-4) of a care facility. Each patient room (Rooms 1-4) includes at least one patient care system 12 including a dedicated power line network 16 creating a local connective network. Rooms 1-3 each illustratively include a single patient care system $12_i$, $12_j$, $12_k$ including a respective patient support device $14_i$, $14_j$, $14_k$ and powerline network $16_i$, $16_j$, $16_k$, and Room 4 illustratively includes two patient care devices $12_x$, $12_y$ each including respective a patient support device $14_x$, $14_y$ and each with its own respective powerline network $16_x$, $16_y$. Each patient support device 14 includes an indicator 50 that communicates a pattern, for local observation, that is based on the patient ID of the patient assigned to the particular patient support device 14 in each room. Because the patterns are based on the unique patient ID's, the pattern of each patient support device $14_i$, $14_j$, $14_k$, $14_x$, $14_y$ is unique to the assigned patient.

For example, in Room 1, $patient_i$ is assigned to patient support device $14_i$. Based on the unique patient ID of $patient_i$, indicator $50_i$ illustratively communicates three short flashes before a pause, and repeats. In Room 2, $patient_j$ is assigned to patient support device $14_j$. Based on the unique patient ID of $patient_j$, indicator $50_j$ communicates one long flash before one short flash, and repeats. In Room 3, $patient_k$ is assigned to patient support device $14_k$. Based on the unique patient ID of $patient_k$, indicator $50_k$ communicates two long flashes before a pause, and repeats. These flash sequences are, of course, just to give some possible examples and it should be appreciated that all flashing sequences are intended to be within the scope of this disclosure.

In the illustrative embodiment as shown in FIG. 2, when patient care apparatus 24 receives a signal indicating a patient ID from power line network 16, the indicator 25 of the patient care apparatus 24 communicates a pattern for local observation that is based on the received signal. For example, in Room 1 patient care apparatus $24_i$ is connected to power line network $16_i$ and receives the signal indicating the unique patient ID of patient therefrom. Based on the signal indicating the patient ID of patient, indicator $25_i$ communicates three short flashes before a pause, and repeats. In Room 2, patient care apparatus $24_j$ is connected to power line network $16_j$ and receives a signal indicating the unique patient ID of $patient_j$ therefrom. Based on the signal indicating the patient ID of $patient_j$, indicator $25_j$ communicates one long flash before one short flash, and repeats. In Room 3, patient care apparatus $24_k$ is not presently connected to power line network $16_k$ but was recently connected thereto and received a signal indicating the unique patient ID of $patient_k$ therefrom. Based on the previously received signal indicating the patient ID of $patient_k$, indicator $25_k$ communicates two long flashes before a pause, and repeats. Again, the flash sequences just described are simply to give some possible examples and all possible flash sequences are intended to be within the scope of this disclosure. It should be appreciated that devices 14 and apparatuses 24 coupled to the same network 16 have substantially synchronous flash sequences based on patient ID.

Figure 3:
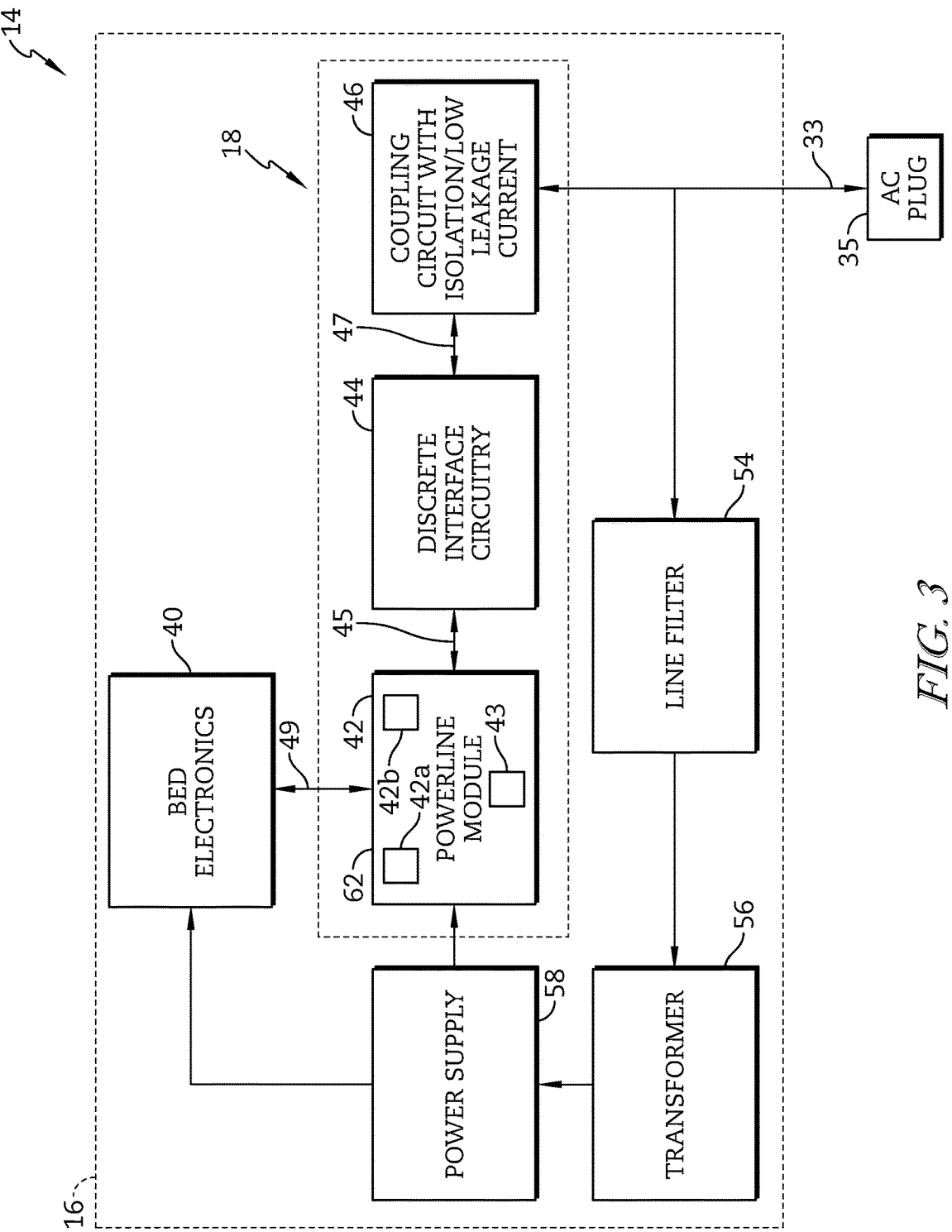
FIG. 3 is diagrammatic view of a portion of a power line network including circuitry for receiving electrical power and communicating information such as a patient ID.

As shown in FIG. 3, Room 4 includes a number of patient care devices $12_x$, $12_y$. Patient care system $12_x$ includes patient support $14_x$ and power line network $16_x$. $Patient_x$ is assigned to patient support device $14_x$. Based on the unique patient ID of $patient_x$, indicator $50_x$ illustratively communicates one short flash before one long flash, and repeats. Patient care apparatus $24_x$ is connected to power line network $16_x$ and receives a signal indicating the unique patient ID of $patient_x$ therefrom. Based on the signal indicating the patient ID of $patient_x$, indicator $25_x$ communicates one short flash before one long flash, and repeats. The patterns of indicators $25_x$, $50_x$ are synchronized such that a local observer can recognize their correspondence.

Patient care system $12_y$ includes patient support $14_y$ and power line network $16_y$. $Patient_y$ is assigned to patient support device $14_y$. Based on the unique patient ID of $patient_y$, indicator $50_y$ illustratively communicates two short flashes before one long flash, and repeats. Patient care apparatus $24_y$ is not connected to power line network $16_y$ and stores information from a previously received signal indicating a unique patient ID of $patient_u$ from a previous communication. Based on the previously received signal indicating the patient ID of $patient_u$, indicator $25_y$ communicates three short flashes before one long flash, and repeats. The patterns of indicators $25_y$, $50_y$ are not synchronized such that a local observer can recognize their lack of correspondence. A caregiver can easily observe that the information known to patient care apparatus $24_y$ does not properly correspond to $patient_y$ and is alerted to the inconsistency by visual observation of the disparate flash sequences.

Returning now to the illustrative embodiment of FIG. 1, patient support device 14 is illustratively embodied as a hospital bed including a frame 30 and mattress or support surface 32. In some embodiments, patient support device 14 is a patient table, chair, and/or any other type of patient support. As discussed below, patient support device 14 includes a bed electronics module 40 (FIG. 3) that includes various electronic devices including devices configured to receive and store a patient ID, and to transmit a signal indicating the patient ID. A patient occupying patient support device 14 is associated therewith by reception of the patient ID of the patient by the patient support device 14. In the illustrative embodiment, ID source device 18 of power line network 20 is attached to frame 30 and receives and stores the patient ID as shown in FIG. 1.

ID source device 18 of power line network 20 is illustratively embodied as a communication module configured to receive and store the patient ID and to communicate a signal indicating the stored patient ID over the power line network 20. ID source device 18 is illustratively configured to receive the patient ID from bed electronics module 40 for communication over power line network 16.

ID source device 18 is illustratively connected for communication with bed electronics module 40 of patient support device 14 as shown in FIG. 3. Bed electronics module 40 illustratively represents various patient support device electronics other than those depicted in FIG. 3, for example, operational motors such as bed height and mattress support deck position motors; user inputs such as buttons, switches, graphical display and interfaces; communication and networking devices such hospital network transceivers and nurse call components; as well as other components such as sensors, processors, memory devices, and various discrete circuit components associated therewith. Although represented as a single module, bed electronics module 40 represents any number of components arranged for patient support device operation.

In the illustrative embodiment, ID source device 18 receives a patient ID from network 22 through bed electronics module 40. The patient ID is a unique identification code that is assigned to a patient of the care facility. In the illustrative embodiment, the patient ID is associated with the particular patient support device 14 by storage and association with a patient support device ID unique to the particular patient support device 14, within a database of network 22, for example, a relational database 64 as suggest in FIG. 1. In some embodiments, the patient ID is received by patient support device 14 by being entered into the bed electronics module 40 by a user, such as a caregiver, directly through a user interface of bed electronics module 40, by scanning an ID badge of the patient such as a wristband of the patient, by wired and/or wireless local detection from a patient badge, and/or by any other local communication manner with patient support device 14.

In the illustrative embodiment, patient support device 14 communicates with the network 22 of the care facility to communicate information therebetween (illustratively represented by two-way communication lines 52 in FIG. 1), for example, the patient ID and/or the location of the patient support device 14 as suggested in FIG. 1. Communications between patient support device 14 and network 22 are illustratively embodied to include indication of the patient support device ID to enable correct dispatching of various patient support devices 24 within the facility. In the illustrative embodiment, communications between network 22 and patient support device 14 include wireless communications using a Bluetooth® protocol, but in some embodiments include Wi-Fi (IEEE 802.11b/g/n), WiMax (IEEE 802.16e), Zigbee (e.g., 802.15.4), mobile communications technologies such as 3G or 4G technology, radio frequency (RF), and/or other wireless protocols, hardwired communications, and/or combinations thereof. Hardware and/or software required to facilitate the described communications between patient support device 14 and network 22 is illustratively incorporated within network 22, but in some embodiments is at least partially incorporated into patient support device 14.

Bed electronics module 40 illustratively receives and stores a patient ID from network 22. Bed electronics module 40 illustratively communicates the patient ID to ID source device 18. In the illustrative embodiment, bed electronics module 40 periodically updates ID source device 18 with the patient ID, including immediately upon receiving a new patient ID from network 22. In some embodiments, ID source device 18 sends a request to bed electronics module 40 for an updated patient ID.

ID source device 18 receives and stores the patient ID from bed electronics module 40. ID source device 18 is illustratively configured to communicate a signal indicating the patient ID over the power line network 20. In the illustrative embodiment as shown in FIG. 3, ID source device 18 includes a power line transceiver 42, discrete interface circuitry 44, and a coupling circuit 46. Power line transceiver 42 operates similar to that disclosed in U.S. Patent Application 2013/0069771, the entire contents of which are incorporated by reference including at least the arrangements of power line transceivers and associated components.

Power line transceiver 42 illustratively includes frequency shift keying modulators/demodulators (modems) indicated by numeral 43 in FIG. 3. In some embodiments, power line transceiver 42 includes modulator/demodulators and any other associated hardware and software configured for other types of signal modulation such as various key shifting techniques for example amplitude, binary, multiple phase, amplitude-phase, and combinations such as quadrature amplitude modulation; multiplexing techniques, for example, frequency-division and orthogonal frequency division; and/or combinations thereof.

Power line transceiver 42 illustratively includes a processor 42a and memory device 42b as shown in FIG. 3. Memory device 42b is configured to store the received patient ID and instructions for determining the pattern based on the patient ID. Processor 42a is configured to receive the patient ID from bed electronics module 40 and store patient ID on the memory device 42a for retrieval, to execute the instructions stored on the memory device 42a using the patient ID to determine the pattern, and to operate light source 50b to communicate the determined pattern. In the illustrative embodiment, the instructions include an algorithm. In some embodiments, the instructions include a lookup table, decision matrix, and/or any other manner of determining a distinct pattern based on a patient ID.

Patient support device 14 illustratively includes a line filter 54, transformer 56, and power supply 58 as shown in FIG. 3. Line filter 54 is electrically connected to power cord 33 and plug 35 of patient support device 14. Line filter 54 has an output connected to transformer 56, and transformer 56 has an output connected to power supply 58. Transformer 56 reduces the amplitude of incoming alternating current (AC) voltage (120v) from electrical power circuit 20 and provides electrical isolation. Power supply 58 illustratively converts the stepped down power to direct current (DC) at the levels required for use by bed electronic module 40, power line transceiver 42, and any other patient support device electrical needs.

In the illustrative embodiment, power line transceiver 42 is connected for bidirectional communication with bed electronics module 40 by line 49. Power line transceiver 42 is connected for bidirectional communication with discrete interface circuitry 44 as indicated by line 45. Discrete interface circuitry 44 is connected with coupling circuit 46 with isolation and/or low leakage current for bi-directional communication as indicated by line 47. Coupling circuit 46 is electrically connected with at least one conductor of power cord 33 for bidirectional communication. Power cord 33 transmits electric power from electrical circuit 20 to patient support device 14 and communicates data therebetween through at least one modulated carrier signal as suggested in FIG. 1. Plug 35 of power cord 33 illustratively connects to outlet 37 of electrical circuit 20.

In the illustrative embodiment, indicator 25 of patient care apparatus 24 includes an indicator module 25a configured to receive the signal indicating a patient ID and to operate indicator light source 25b to produce a pattern based on the received signal. Indicator module 25a illustratively includes a processor 25c, and a memory device 25d. Memory device 25d illustratively stores information indicated by the signal and instructions for determining the pattern based on the information indicated by the signal. Processor 24c is configured to determine the information from the signal and to execute the instructions stored on the memory device 24d to determine the pattern based on the information indicated by the signal. In the illustrative embodiment, the instructions include an algorithm. In some embodiments, the instructions include a lookup table, decision matrix, and/or any other manner of determining a distinct pattern based on a patient ID. In the illustrative embodiment, indicator module 25a receives a signal including the patient ID from the ID source device 18 and determines the pattern based on the patient ID received. Indicator 50 operates similarly to indicator 25 but shares memory 42b and processor 42a components with power line transceiver 42 such that no distinct indicator module is required, but in some embodiments includes a distinct indicator module. Synchronizing the timing between equal patterns of indicator 25 and indicator 50 is illustratively achieved by coordination based on the carrier signal of the power line network 20 and the power line network 16 is configured to account for timing effects of signal transmission.

Electrical circuit 20 is illustratively embodied as being disposed within a panel wall 64 of the care facility as shown in FIGS. 1 and 2. Electrical circuit 20 is embodied as connected to the electrical power grid of the care facility to receive power therefrom. In some embodiments, power line network 16 includes signal isolation and/or conditioning equipment configured to limit the range of communications to the immediate vicinity of each power line network 16 such that a local connective network is established for communication across power line network 16, but does not carry into other networks (including other power line networks 16) whether electrically and/or otherwise connected to the electrical circuit 20.

In the illustrative embodiment, power line network 16 communicates a signal including the patient ID to the patient care apparatus 24. In some embodiments, the signal includes the pattern as determined by the power line transceiver 42 of ID source device 18, and indicator module 25a is configured to receive, store, and execute the pattern as received.

In the illustrative embodiment, the indicators 25, 50 are embodied as communicating patterns by light sources 25b, 50b for generating flashes. In some embodiments, the indicators 25 include audio devices for communicating an audio pattern, communicate patterns by varying the color of light sources 25b, 50b, and/or other configuration for local indication, and/or combinations thereof.

In the illustrative embodiment, patient care apparatus 24 receives the patient ID and is communicatively coupled to the patient support device 14 through the power line network 16. In some embodiments, patient care device 24 is configured to transmit data through power line network 16 to patient support device 14. In some embodiments, the data (for example the patient ID) is communicated to the patient care apparatus 24 by wired and/or wireless signals sent from patient care device 14, power line network 16, network 22, any other communication source, and/or any combination thereof. As described above, patient care apparatus 24 can at times be disconnected from electrical circuit 20 and illustratively includes a battery power storage for operational power when it is not plugged into any electrical circuit 20. In some embodiments, a patient ID is entered manually into the patient care apparatus 24 via a user interface, by scanning a patient badge such as a wristband of the patient, by wired and/or wireless local detection from a patient badge, and/or by any other local communication manner.

Power line network 16 is illustratively embodied to communicate the patient ID, but in some embodiments is configured to communicate any sort of data therethrough. For example, in some embodiments, the power line 16 network is configured to communicate a variety of patient information such as patient name, age, weight, height, medical condition, treatment, assigned location, risk status, and/or any combination thereof and/or pairing content such as code names, code numbers, distinctive colors, distinctive sequences, and/or combinations thereof.

The present disclosure includes smart patient care environments. Such environments may include medical device connectivity including bi-directional communication between medical devices and an electrical medical record which has numerous benefits including protection of patients from medical errors and improved care efficiency. Device connectivity may depend on accurate and timely patient identification and/or association, but creating a digital association between data items that mirrors the association that exists in the physical world continues to challenge existing solutions. Known devices may include active (e.g., barcode, RFID) or passive based on remote mapping (e.g., through location based ADT). The present disclosure includes creation of a necessary association through passive association based on local mapping, by embedding the patient's ID within the power network used by her medical devices. It may build a data-over-network technology to create a personal power and data network within a particular patient care environment, populate that network with the patient's unique identification number, and make that ID number readable and/or available to devices connected to that system. Devices connected to that system will know which patient it should be associated with, creating and ensuring an accurate association between the device and patient even within EMR.

The present disclosure includes a power line network ("PLN") created to encompass a network of power outlets within a specific patient environment. One device (the "ID transmitting device") connected to the PLN may receive a unique identifier designating the patient under care in that patient care environment (the "Patient ID"), and then transmit that Patient ID on the PLN. Other devices (the "ID Receiving Devices") may receive the Patient ID from the PLN, and may use that Patient ID as the key to associate any data they transmit with the patient associated with that Patient ID. By embedding the patient's ID within the power network used by her medical devices, the system and/or device can combine the advantages of an active (accuracy, timeliness) and passive (ease of use, reduction in errors) based system and/or device. By enabling the accurate, timely association of medical devices with a patient, the innovation can allow care facilities, such as hospitals, to take advantage of the benefits of medical device connectivity (e.g., improved workflow through automated documentation, avoidance of errors created by erroneous communication of data contained within EMR, identification of patient safety risks such a medication errors, early detection of patient deterioration.).

The present disclosure includes creating a digital association between records to mirror the association that exists in the physical world. Medical Device Connectivity has numerous potential benefits. Medical Device Connectivity may include the transfer of data (and the use of that data for analysis, control, or notification purposes) between (1) a device and a patient's Electronic Medical Record ("EMR"), (2) the EMR and a device, and/or (3) different devices. This connectivity has numerous benefits such as increased efficiency and accuracy of documentation through process automation (e.g., patient vital signs logged in real time to the patient's medical record) and enhanced patient safety through clinical decision support based on that data (e.g., recognition of a medication error based on knowledge of the drug being delivered to a patient via IV and the allergy to that medication based on the patient's medical record). Improved accuracy and timeliness of this association can improve conditions. If a device is associated with the wrong patient, decisions will be made based on erroneous data. If that association is delayed, events that could have been addressed during that time lag cannot be addressed. Current Patient Identification & Association solutions have significant limitations. Relational association by reference to an ADT (Admission, Discharge and Transfer) system based on location alone can be hampered by the lack of timely and accurate data in that ADT system. A patient may frequently be in a room different than that shown by the ADT system, for reasons including transfer or redirection within a unit based on equipment needs, delayed discharges or transfers, or other workflow challenges. Some check systems can create the frequent circumvention of the system by caregivers and the workflow challenges associated by creating the association each time the device is used. The shortcomings of this type of system are evident from their lack of widespread adoption more than 30+ years since their launch.

The present disclosure includes "Data Over Power" (also referred to as power-line communication or PLC) which is a system that simultaneously transmits power and data over a single wired network. In this system, a device connected to a power-line network ("PLN") can send and receive data to another device connected to that PLN, at the same time as both devices receive electricity from that PLN. One non-limiting example of such a system is a home automation system—a modified light switch connected to a home's electrical wiring can modulate a carrier wave (of between 20 and 200 kHz) to transmit data to control lamp connected to a power outlet on that system.

The present disclosure includes Power Line Networks ("PLN") that includes a network of power outlets within a specific patient environment. In one non-limiting example, the network is comprised of all power outlets in the patient room (for example, those in the headwall system). In another non-limiting example, the network includes the auxiliary outlet resident on the patient bed, available to power devices such as ventilators, IV pumps, vital sign monitors, etc. One device (the "ID Transmitting Device") connected to that PLN can receive a unique identifier designating the patient under care in that patient environment (the "Patient ID"), and then transmit that Patient ID onto the PLN. In some embodiments, the ID Transmitting Device is a bed, which can receive the patient's unique identifier via a number of methods, including manual entry, barcode scanning, RFID scanning without common issues associated therewith. Numerous other devices could serve as ID Transmitting Device, including a dedicated wall module, the nurse call touchscreen, or a bedside touchscreen, and could be augmented by other sensors to provide knowledge of patient location such as RTLS, motion detectors, or machine vision systems. Other devices (the "ID Receiving Devices") will receive the Patient ID from the PLN, and will then use that Patient ID as the key to associate any data they transmit with the patient associated with that Patient ID.

In the present disclosure, the patient's name may not be required for indication but rather just that the person in the EMR and the person in the bed are the same person, a "paired" visual cue (e.g., lights flashing in sequence) would alert the caregiver to an association error. A smart care environment results including devices with interconnectivity which can effectively create an association between the device and the patient. A non-limiting example includes an infusion pump recording information regarding the drug to be delivered to a patient, the device and/or system must know which patient is associated with that specific infusion pump. There are challenges in creating that association in the prior art. Both automated and manual methods of creating an association can result in errors.

Mistakes can occur under assumption that the Admission-Discharge-Transfer (ADT) system can be used to create that association (for example that a patient John Doe is in Room 103 and any device in Room 103 should send its information to the medical record for John Doe. But Room 103 may not have been ready when Joe Doe was needing a room and John Doe may have been placed in Room 303 or may have been sent to Room 404 where telemetry is available, etc). Even when the ADT is accurate, it may not be accurate at the exact point in time at which data is required. Errors in data can be difficult to discover. If a caregiver associates a patient with the wrong vital sign monitor, it can be difficult to recognize the error on the basis of the vitals and/or data alone (for example if the data shows a fairly normal heart and respiration rate, it is hard to anticipate the cue that can make the caregiver realize that they have made an error). By creating a visible indication of the association between a patient and device, the likelihood of erroneous association can be reduced along with related errors.

Although certain illustrative embodiments have been described in detail above, variations and modifications exist within the scope and spirit of this disclosure as described and as defined in the following claims.

The invention claimed is:

1. A patient care device, comprising:
a patient support device in a patient room,
a power line network local to the patient room, comprising
an ID source device configured to receive a patient ID associated with a patient assigned to the patient support device and to communicate the patient ID throughout the power line network,
an electric power distribution circuit configured to provide electric power to the patient support device,
at least one power receptacle connected to receive electric power from the electric power distribution circuit,
wherein the power line network communicates the patient ID to the at least one power receptacle using the electric power distribution circuit along with supplying electric power to the at least one power receptacle prior to other devices being connected to the at least one power receptacle so that after being connected to the at least one power receptacle, the other devices receive the patient ID and power through the power line network as a result of being connected to the at least one power receptacle,
a patient care apparatus electrically connected to the electric power distribution circuit to receive electrical power and the patient ID therefrom over the power line network, wherein the patient support device has a first light, the patient care apparatus is spaced from the patient support device and has a second light, and the patient care apparatus is communicatively coupled to the patient support device to provide a visual cue that the patient support device and the patient care apparatus are both associated with the patient by flashing the first and second lights substantially synchronously so that the first and second lights are perceived by an observer as turning on and turning off at the same time.

2. The patient care device of claim 1, wherein the ID source device includes a power line transceiver.

3. The patient care device of claim 1, wherein the ID source device communicates the patient ID throughout the power line network through a modulated carrier signal embedded within the electrical power provided by the electrical power distribution circuit.

4. The patient care device of claim 1, wherein the patient support device is connected for communication with a communication network and receives the patient ID associated with the patient assigned to the patient support device from the network for communication to the ID source device.

5. The patient care device of claim 1, wherein the patient care apparatus is electrically connected to the electric power distribution circuit by connection of a plug of the patient care apparatus to the at least one power receptacle.

6. The patient care device of claim 5, wherein the at least one power receptacle is mounted to the patient support device.

7. The patient care device of claim 1, wherein the patient support device includes an indicator configured to communicate a unique pattern indicating the patient ID to provide locally observable identification of the patient ID.

8. The patient care device of claim 7, wherein the indicator includes a light source configured to flash to communicate the pattern.

9. The patient care device of claim 1, wherein the patient support device and the patient care apparatus are communicatively coupled by the power line network.

10. The patient care device of claim 9, wherein the flashing of the first and second lights substantially synchronously results from the patient ID being known to the patient care apparatus and known to the patient care device.

11. A patient care device, comprising:
a patient support device,
a power line network, comprising
   an ID source device configured to receive a patient ID associated with a patient assigned to the patient support device and to communicate the patient ID throughout the power line network,
   an electric power distribution circuit configured to provide electric power to the patient support device,
   at least one power receptacle connected to receive electric power from the electric power distribution circuit, wherein the power line network communicates the patient ID by configuration of the electric power distribution circuit to supply electric power to operate devices connected to the at least one power receptacle, and
a patient care apparatus electrically connected to the electric power distribution circuit to receive electrical power and the patient ID therefrom over the power line network,
wherein the patient support device has a first light, the patient care apparatus is spaced from the patient support device and has a second light, and the patient care apparatus is communicatively coupled to the patient support device to provide a visual cue that the patient support device and the patient care apparatus are both associated with the patient by flashing the first and second lights substantially synchronously so that the first and second lights are perceived by an observer as turning on and turning off at the same time,
wherein the patient support device and the patient care apparatus are communicatively coupled by the power line network,
wherein the flashing of the first and second lights substantially synchronously results from the patient ID being known to the patient care apparatus and known to the patient care device.

12. The patient care device of claim 1, wherein the patient support device comprises a patient bed.

13. The patient care device of claim 12, wherein the patient care apparatus comprises one or more of the following: an intravenous (IV) fluid machine, a ventilator, or a patient monitor.

14. The patient care device of claim 1, wherein the patient care apparatus comprises one or more of the following: an intravenous (IV) fluid machine, a ventilator, or a patient monitor.

15. The patient care device of claim 1, wherein the patient support device is configured to communicate with remote computer equipment via a communications network.

16. The patient care device of claim 15, wherein the patient support device is configured to communicate wirelessly with the communications network.

17. The patient care device of claim 1, wherein the patient support apparatus is configured to communicate with remote computer equipment via a communications network.

18. The patient care device of claim 17, wherein the patient support apparatus is configured to communicate wirelessly with the communications network.

* * * * *